(12) United States Patent
Sieracki et al.

(10) Patent No.: US 7,899,546 B2
(45) Date of Patent: Mar. 1, 2011

(54) FAILSAFE PROGRAMMING OF IMPLANTABLE MEDICAL DEVICES

(75) Inventors: Jeffrey M. Sieracki, Silver Spring, MD (US); Richard B. North, Baltimore, MD (US)

(73) Assignee: Medtronic, Inc., Minneapolis, MN (US)

( * ) Notice: Subject to any disclaimer, the term of this patent is extended or adjusted under 35 U.S.C. 154(b) by 310 days.

(21) Appl. No.: 12/038,364

(22) Filed: Feb. 27, 2008

(65) Prior Publication Data

US 2008/0147145 A1 Jun. 19, 2008

Related U.S. Application Data

(62) Division of application No. 10/696,725, filed on Oct. 29, 2003, now Pat. No. 7,373,206.

(60) Provisional application No. 60/422,259, filed on Oct. 31, 2002, provisional application No. 60/503,224, filed on Sep. 15, 2003.

(51) Int. Cl.
*A61N 1/08* (2006.01)
(52) U.S. Cl. ...................................................... 607/60
(58) Field of Classification Search .................... 607/60
See application file for complete search history.

(56) References Cited

U.S. PATENT DOCUMENTS

| | | |
|---|---|---|
| 3,942,535 A | 3/1976 | Schulman |
| 4,208,008 A | 6/1980 | Smith |
| 4,304,238 A | 12/1981 | Fischer |
| 4,365,633 A | 12/1982 | Loughman et al. |
| 4,550,732 A | 11/1985 | Batty, Jr. et al. |
| 4,587,970 A | 5/1986 | Holley et al. |
| 4,926,865 A | 5/1990 | Oman |
| 5,158,078 A | 10/1992 | Bennett et al. |
| 5,226,413 A | 7/1993 | Bennett et al. |
| 5,350,407 A | 9/1994 | McClure et al. |
| 5,383,915 A | 1/1995 | Adams |
| 5,456,692 A * | 10/1995 | Smith et al. ................ 607/31 |
| 5,607,458 A * | 3/1997 | Causey et al. ............... 607/27 |

(Continued)

FOREIGN PATENT DOCUMENTS

EP 0 750 921 A2 1/1997

(Continued)

OTHER PUBLICATIONS

Fowler, K.R., "Neurological Stimulation System", Proceedings AAMI 21st Annual Meeting, Apr. 12-16, p. 27, 1986.

(Continued)

*Primary Examiner*—Michael Kahelin
(74) *Attorney, Agent, or Firm*—Shumaker & Sieffert, P.A.

(57) ABSTRACT

A watchdog unit receives stay-alive signals from a programming device during programming of an implantable medical device. The watchdog unit maintains a watchdog timer, and resets the timer upon receipt of each stay-alive signal. If the watchdog timer expires, the watchdog unit changes a mode of operation of the implantable device, e.g., places the implantable medical device into a known, safe state. For example, the watchdog unit may cause the implantable medical device to suspend delivery of therapy, perform a power-on reset, and/or recall a known, safe, therapy delivery program.

12 Claims, 7 Drawing Sheets

U.S. PATENT DOCUMENTS

| | | | |
|---|---|---|---|
| 5,615,318 | A | 3/1997 | Matsuura |
| 5,653,735 | A * | 8/1997 | Chen et al. .................. 607/9 |
| 5,683,432 | A | 11/1997 | Goedeke et al. |
| 5,690,690 | A | 11/1997 | Nappholz et al. |
| 5,752,977 | A | 5/1998 | Grevious et al. |
| 5,792,201 | A | 8/1998 | Causey, III et al. |
| 5,938,690 | A | 8/1999 | Law et al. |
| 6,308,102 | B1 | 10/2001 | Sieracki et al. |
| 6,480,745 | B2 | 11/2002 | Nelson et al. |
| 6,577,899 | B2 | 6/2003 | Lebel et al. |
| 6,597,951 | B2 | 7/2003 | Kirsch et al. |
| 6,609,032 | B1 | 8/2003 | Woods et al. |
| 6,622,045 | B2 | 9/2003 | Snell et al. |
| 6,654,027 | B1 | 11/2003 | Hernandez |
| 6,659,968 | B1 | 12/2003 | McClure |
| 6,665,565 | B1 | 12/2003 | Stomberg et al. |
| 6,868,309 | B1 | 3/2005 | Begelman |
| 6,878,112 | B2 | 4/2005 | Linberg et al. |
| 6,978,181 | B1 | 12/2005 | Snell |
| 7,015,935 | B2 | 3/2006 | Herget et al. |
| 7,043,305 | B2 | 5/2006 | KenKnight et al. |
| 7,060,031 | B2 | 6/2006 | Webb et al. |
| 7,065,409 | B2 | 6/2006 | Mazar |
| 7,155,290 | B2 | 12/2006 | Von Arx et al. |
| 7,489,970 | B2 | 2/2009 | Lee et al. |
| 7,610,099 | B2 | 10/2009 | Almendinger et al. |
| 7,657,319 | B2 | 2/2010 | Goetz et al. |
| 2002/0016568 | A1 | 2/2002 | Lebel et al. |
| 2002/0049480 | A1* | 4/2002 | Lebel et al. .................. 607/60 |
| 2002/0123673 | A1 | 9/2002 | Webb et al. |
| 2002/0133207 | A1 | 9/2002 | Thomas et al. |
| 2003/0088290 | A1 | 5/2003 | Spinelli et al. |
| 2004/0138724 | A1 | 7/2004 | Sieracki et al. |
| 2004/0199215 | A1 | 10/2004 | Lee et al. |
| 2004/0260363 | A1 | 12/2004 | Arx et al. |
| 2005/0277999 | A1 | 12/2005 | Strother et al. |
| 2005/0283198 | A1 | 12/2005 | Haubrich et al. |
| 2006/0161213 | A1 | 7/2006 | Patel |
| 2006/0190047 | A1 | 8/2006 | Gerber et al. |
| 2008/0140161 | A1 | 6/2008 | Goetz et al. |
| 2008/0140162 | A1 | 6/2008 | Goetz et al. |
| 2009/0157137 | A1 | 6/2009 | Gilkerson et al. |

FOREIGN PATENT DOCUMENTS

| | | |
|---|---|---|
| EP | 0 753 327 A2 | 1/1997 |
| WO | WO 02/057994 A2 | 7/2002 |
| WO | WO 03/092769 A2 | 11/2003 |

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., "Consensus conference on the neurosurgical management of pain," Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation for Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

Khalessi, A. A., Taylor, R. S., Brigham, D. D., North, R. B., "Automated, patient-interactive spinal cord stimulator adjustment: A cost-minimization analysis," Neurosurgery, 53:501-502, Aug. 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, Mar. 2003.

U.S. Appl. No. 10/696,501, entitled "Implantable Neurostimulator Programming with Battery Longevity Indication", filed Oct. 29, 2003, Richard B. North, Kim R. Fowler, Jeffrey M. Sieracki, David D. Brigham.

U.S. Appl. No. 10/696,781, entitled "Neurostimulation Therapy Manipulation", filed Oct. 29, 2003, Richard B. North, Jeffrey M. Sieracki.

U.S. Appl. No. 10/696,494, entitled "Distributed System for Neurostimulation Therapy Programming", filed Oct. 29, 2003, Richard B. North, Kim R. Fowler, Jeffrey M. Sieracki.

U.S. Appl. No. 10/696,491, entitled "Body Region Indication", filed Oct. 29, 2003, Richard B. North, Jeffrey M. Sieracki.

U.S. Appl. No. 10/696,778, entitled "Applying Filter Information to Identify Combinations of Electrodes", filed Oct. 29, 2003, Richard B. North, Jeffrey M. Sieracki.

PCT International Search Report for PCT/US/03/34325, mailed Apr. 2, 2004.
Reply to Written Opinion for patent application No. PCT/US2007/024096, filed Sep. 5, 2008, 14 pages.
Reply to Written Opinion for patent application No. PCT/US2007/023817, filed Sep. 30, 2008, 12 pages.
Office Action from U.S. Appl. No. 11/940,573, dated Apr. 5, 2010, 22 pp.
Response to Office Action dated Apr. 5, 2010, from U.S. Appl. No. 11/940,573, filed Jul. 6, 2010, 11 pp.
Office Action from U.S. Appl. No. 11/940,604, dated Apr. 5, 2010, 20 pp.
Response to Office Action dated Apr. 5, 2010, from U.S. Appl. No. 11/940,604, filed Jul. 6, 2010, 17 pp.

* cited by examiner

FAILSAFE PROGRAMMING OF IMPLANTABLE MEDICAL DEVICES

This application is a divisional of U.S. application Ser. No. 10/696,725, filed Oct. 29, 2003 U.S. Pat. No. 7,373,206, which claims the benefit of U.S. provisional application Ser. No. 60/422,259, filed Oct. 31, 2002, and U.S. provisional application Ser. No. 60/503,224, filed Sep. 15, 2003. The entire content of each of these applications is incorporated herein by reference.

TECHNICAL FIELD

The invention relates to medical devices, and more particularly, to programming of implantable medical devices.

BACKGROUND

A variety of types of implantable medical devices are used to deliver therapies to patients. For example, implantable pulse generators are used to deliver neurostimulation and cardiac pacing therapies to patients. As another example, implantable pumps are used to deliver therapeutic agents to patients.

Typically, a clinician uses a programming device, e.g., a clinician programmer, to program aspects of the operation of an implantable medical device after it has been implanted in a patient. Programming devices are computing devices capable of communicating with implantable medical devices through patient body tissue via device telemetry. To facilitate communication with an implantable medical device, a programming device may be coupled to a programming head that is placed on the surface of the patient at a position proximate to location of the implantable medical device within the patient.

A trend in the implantable medical device arts is the ever-increasing complexity of the devices themselves, and the firmware that controls the operation of the devices. For example, many modern implantable medical devices provide a variety of therapy delivery and/or patient monitoring modes, which may be selected and configured by the clinician during a programming session. During a programming session, the clinician may also need to select values for a variety of programmable parameters, threshold values, or the like, that control aspects the delivery of therapy.

Consequently, programming devices, and more particularly the software that allows a clinician to select modes and/or values for programmable parameters, have become increasingly complex. Programming sessions may involve trial-and-error testing of various modes and/or parameter values. In some cases, a programming session may be automated or semi-automated, e.g., conducted by a clinician or patient, with an algorithm executed by the programming device controlling at least some of the selection of new modes and/or parameter values to test. Such testing requires frequent telemetry communication between the programming device and the implantable medical device as new modes and/or parameters selected by the clinician, the patient, or an algorithm are communicated from the programming device to the implantable medical device.

It is possible for the complex programming software executed by programming devices to have hidden failure modes that do not become apparent, even with extensive validation and testing. It is also possible for the physical cable between a programming device and a telemetry head, the telemetry head itself, or the RF telemetry link between the programming device and the implantable medical device to fail. If one or more such failures occur during a programming session, e.g., during communication of a new mode or new parameter values to the implantable medical device, the incomplete and/or inaccurate transfer of data may leave the implantable medical device operating in an undesirable and potentially unsafe configuration. Moreover, because of the failure of communication between the programming device and the implantable medical device, a clinician may be left with no immediate means to remove the implantable medical device from the unsafe condition.

SUMMARY

In general, the invention is directed toward techniques for failsafe programming of implantable medical devices (IMDs). A watchdog unit receives stay-alive signals from a programming device during programming of an IMD. The watchdog unit maintains a watchdog timer, and resets the timer upon receipt of each stay-alive signal. If the watchdog timer expires, the watchdog unit changes a mode of operation of the implantable device, e.g., places the implantable medical device into a known, safe state, to avoid the IMD being left in an undesirable and potentially unsafe state with no immediate means to remove it from such a state. For example, the watchdog unit may cause the implantable medical device to suspend delivery of therapy, perform a power-on reset, and/or recall a known, safe, therapy delivery program.

The watchdog unit may be located on a cable that connects the programming device to a telemetry head used to communicate with the IMD, may couple the cable to the telemetry head, may be located within the telemetry head, or may be located within the IMD. Consequently, in some embodiments, the stay-alive signals may be active transitions of a data line of the data cable, or wireless telemetry signals. The watchdog unit may be embodied as hardware, a software module, or a combination of hardware and software.

In one embodiment, the invention is directed to a method in which stay-alive signals are received from a programming device during the course of a wireless telemetry session between the programming device and an IMD, and a watchdog timer is reset in response to receipt of each of the stay-alive signals. A mode of operation of the IMD is changed in response to expiration of the watchdog timer.

In another embodiment, the invention is directed to a device that includes a telemetry circuit and a processor. The processor receives stay-alive signals from a programming device during the course of a wireless telemetry session between the programming device and an IMD, and resets a watchdog timer in response to receipt of each of the stay-alive signals. The processor sends a signal to the IMD via the telemetry circuit to change a mode of operation of the IMD in response to expiration of the watchdog timer.

In another embodiment, the invention is directed to an IMD that includes a telemetry circuit and a watchdog unit. The watchdog unit receives stay-alive signals from a programming device via the telemetry circuit during the course of a wireless telemetry session between the programming device and the IMD, and resets a watchdog timer in response to receipt of each of the stay-alive signals. The watchdog unit changes a mode of operation of the IMD in response to expiration of the watchdog timer.

In another embodiment, the invention is directed to a computer-readable medium containing instructions. The instructions cause a programmable processor to receive stay alive signals from a programming device during the course of a wireless telemetry session between the programming device and an IMD, reset a watchdog timer in response to receipt of each of the stay-alive signals, and change a mode of operation of the IMD in response to expiration of the watchdog timer.

In another embodiment, the invention is directed to a method in which programming signals that affect the operation of an IMD are sent to the IMD via wireless telemetry during a programming operation, and stay-alive signals are sent to a watchdog unit during the programming operation to allow the watchdog unit to detect failure of a wireless telemetry session between a programming device and the IMD during the programming operation.

In another embodiment, the invention is directed to a programming device that includes a telemetry circuit and a processor. The processor sends programming signals that affect the operation of an IMD to the IMD via the telemetry circuit during a programming operation, and sends stay-alive signals to a watchdog unit during the programming operation to allow the watchdog unit to detect failure of a wireless telemetry session between the programming device and the IMD during the programming operation.

In another embodiment, the invention is directed to a computer-readable medium containing instructions. The instructions cause a programmable processor to send programming signals that affect operation of an IMD to the IMD via wireless telemetry during a programming operation, and send stay-alive signals to a watchdog unit during the programming operation to allow the watchdog unit to detect failure of a wireless telemetry session between a programming device and the IMD during the programming operation.

The invention may provide advantages. For example, a watchdog unit according to the invention may quickly remove an IMD from an undesirable and unsafe state caused by a failure during programming of the IMD. By maintaining a watchdog timer and resetting the watchdog timer upon receipt of stay-alive signals, a watchdog unit according to the invention may detect hardware or software failures of the programming device, and failure of the cable that couples the programming device to the telemetry head. In embodiments where the watchdog unit is located within the IMD, which are preferred, the watchdog unit may additionally detect failure of the telemetry head, the radio-frequency telemetry connection between the telemetry head and the IMD, and telemetry circuitry of the IMD. However, embodiments wherein the watchdog unit is located outside the IMD may advantageously be used during programming of existing IMDs.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
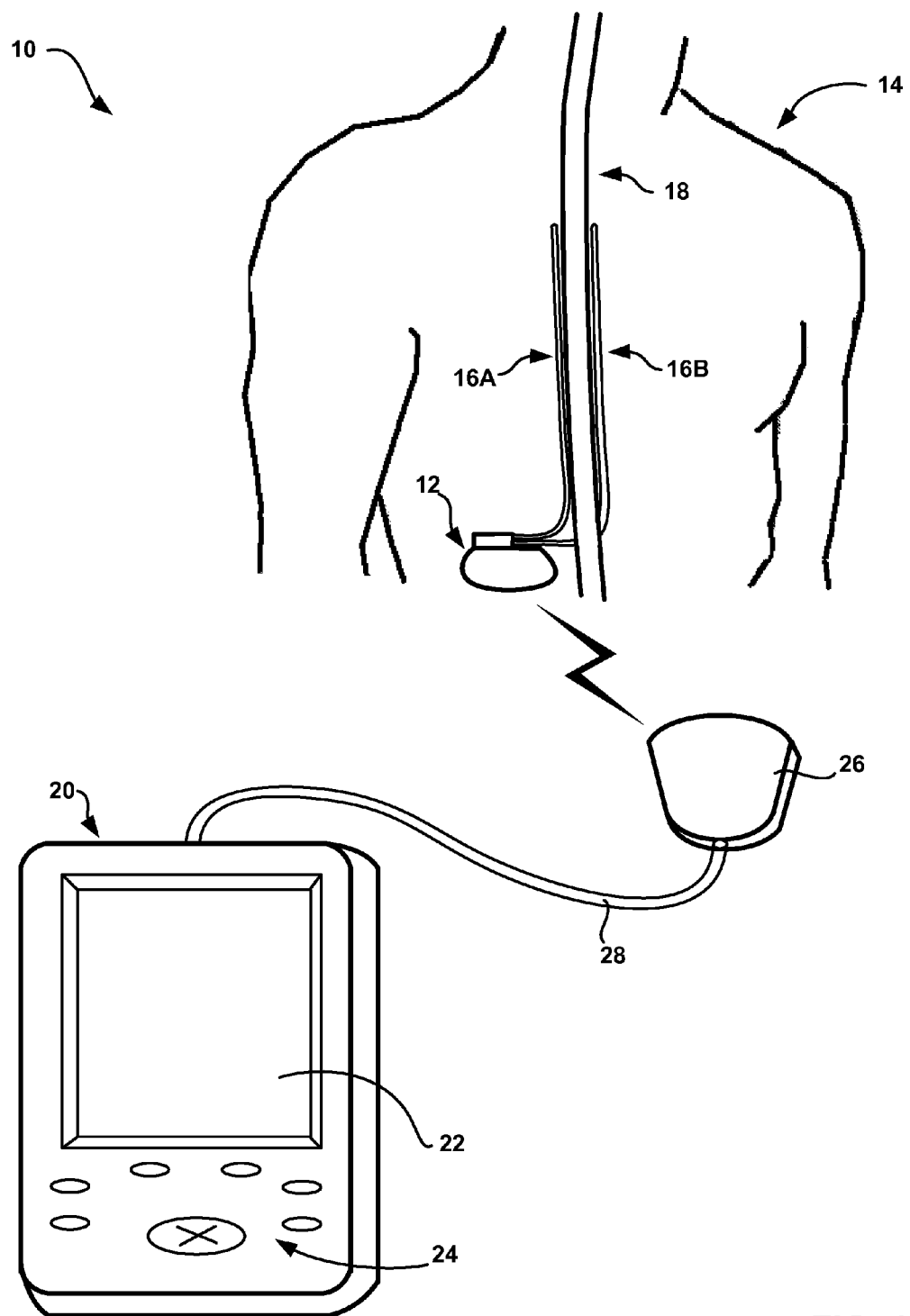
FIG. 1 is a conceptual diagram illustrating a system in which an example implantable medical device is programmed using failsafe programming techniques according to the invention.

FIG. 1 is a conceptual diagram illustrating a system 10 in which an example implantable medical device (IMD) 12 is programmed using failsafe programming techniques according to the invention. IMD 12 is shown in FIG. 1 implanted within a patient 14. In the illustrated embodiment, IMD 12 takes the form of an implantable neurostimulator (INS) that delivers neurostimulation therapy to patient 12 via leads 16A and 16B (hereinafter "leads 16").

Specifically, in the illustrated configuration, leads 16 are implanted proximate to the spinal cord 18 of patient 14, and IMD 12 delivers spinal cord stimulation (SCS) therapy to patient 14 in order to, for example, reduce pain experienced by patient 14. Leads 16 include electrodes (not shown in FIG. 1), and IMD 12 delivers neurostimulation to spinal cord 18 via the electrodes. IMD 12 may be an implantable pulse generator, and may deliver neurostimulation to spinal cord 18 in the form of electrical pulses.

IMD 12 delivers neurostimulation according to a program. The program may include values for a number of parameters, and the parameter values define the neurostimulation therapy delivered according to that program. In embodiments where IMD 12 delivers neurostimulation therapy in the form of electrical pulses, the parameters may include voltage or current pulse amplitudes, pulse widths, pulse rates, and the like. Further, the parameters for a program include information identifying which electrodes have been selected for delivery of pulses according to the program, and the polarities of the selected electrodes.

System 10 also includes a programming device 20. Programming device 20 may, as shown in FIG. 1, be a handheld computing device. Programming device 20 includes a display 22, such as a LCD or LED display, to display information to a user. Programming device 20 may also include a keypad 24, which may be used by a user to interact with programming device 20. In some embodiments, display 22 may be a touch screen display, and a user may interact with programming device 20 via display 22. A user may additionally or alternatively interact with programming device 20 using peripheral pointing devices, such as a stylus or mouse. Keypad 24 may take the form of an alphanumeric keypad or a reduced set of keys associated with particular functions.

A clinician (not shown) may use programming device 20 to program neurostimulation therapy for patient 12. In some embodiments, the clinician specifies programs by selecting program parameter values, and tests the specified programs on patient 12. In other embodiments, programming device 20 provides an automated or semi-automated programming routine in which programming device 20 generates programs and tests the generated programs on patients. In such embodiments, either or both of the clinician and patient 14 may interact with programming device 20 during testing of the generated programs. Further, in such embodiments, the clinician may interact with programming device 20 to confirm programs generated by programming device 20 for testing, and/or to select programs from among those automatically tested by programming device. An exemplary programming device that provides a semi-automated programming routine is described in U.S. Pat. No. 6,308,102, issued to Sieracki et al.

In either case, programming device 20 sends each of the programs to be tested to IMD 12 using radio-frequency telemetry techniques known in the art. For example, programming device 20 may send program parameters as commands, and may send other commands necessary to effect reprogramming of IMD 12 via device telemetry. IMD 12 receives and decodes the commands, and stores the program parameters in registers, or the like, for use in defining the neurostimulation delivered to patient 14 according to that program. Programming device 20 is coupled to a telemetry head 26 via cable 28, and head 26 is placed in proximity to IMD 12 to facilitate telemetry communication between programming device 20 and IMD 12.

Programming device 20 sends a number of commands to IMD 12 to reprogram IMD 12 for each program tested during the programming session. In conventional systems, if IMD 12, cable 28, or telemetry head 26 were to fail during the transmission of commands necessary to reprogram IMD 12 for testing of a program, IMD 12 could be left in an undesirable or potentially dangerous state, e.g., could deliver undesirable or potentially dangerous neurostimulation according to an incomplete program. Moreover, in conventional systems, because IMD 12, cable 28, or head 26 had failed, the clinician and/or patient 14 might be left with no immediate means to remove IMD 12 from the undesirable or potentially dangerous state.

System 10, in accordance with the invention, includes a watchdog unit (not shown). The watchdog unit and programming device 20 provide for failsafe programming of IMD 12, as will be described in greater detail below. The watchdog unit may be embodied as a hardware device, as a software algorithm stored within a computer-readable medium and executed by a processor, or as a combination of hardware and software.

The watchdog unit may be located, for example, within telemetry head 26 or along cable 28. In some embodiments, the watchdog unit may couple cable 28 to head 26. In other embodiments, the watchdog unit is located within or provided by IMD 12.

Figure 2:
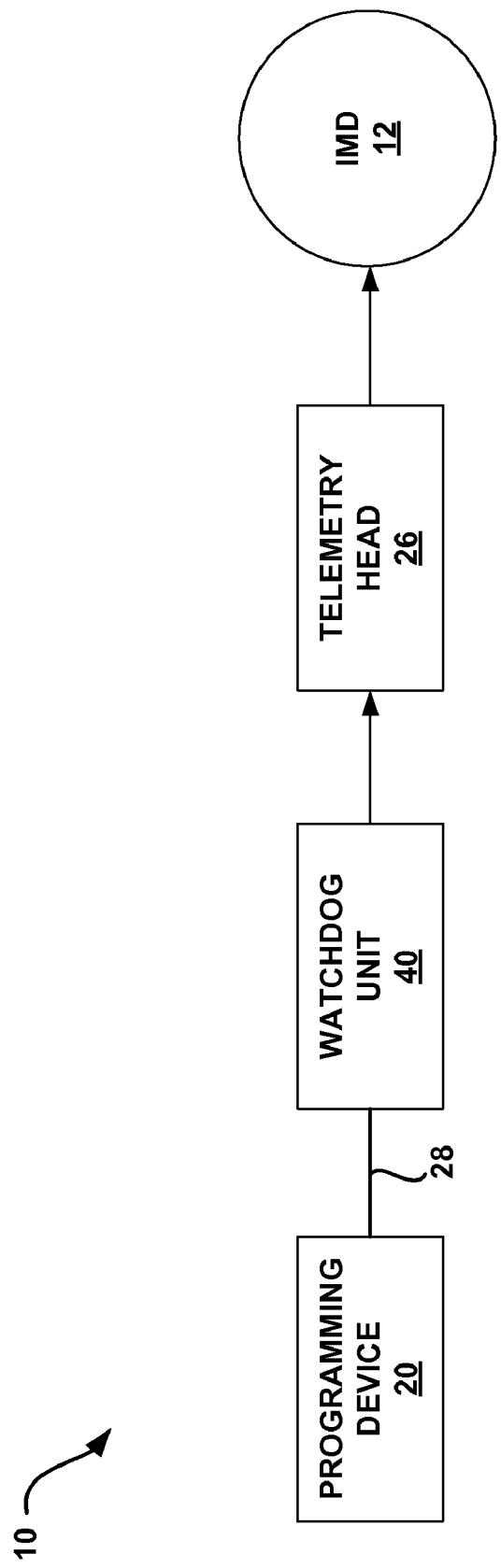
FIG. 2 is a block diagram further illustrating the system of FIG. 1 according to an embodiment of the invention in which the system includes a watchdog unit that facilitates failsafe programming of the implantable medical device of FIG. 1.

FIG. 2 is a block diagram further illustrating system 10 according to an embodiment of the invention. As discussed above, system 10 includes IMD 12, and programming device 20 coupled to telemetry head 26 by cable 28. System 10 further includes a watchdog unit 40, which in the illustrated embodiment couples cable 28 to head 26.

During a programming session, watchdog unit 40 maintains a watchdog timer. Programming device 20 sends stay-alive signals to watchdog unit 40 via cable 28 to indicate that programming device 20 is functioning properly, and watchdog unit 40 resets the watchdog timer in response to each of the stay-alive signals. In the event that watchdog unit 40 fails to receive a stay-alive signal before the watchdog timer expires, watchdog unit 40 sends one or more commands to IMD 12 via telemetry head 26 to change a mode of operation of IMD 12, e.g., to place IMD 12 in a known, safe state.

For example, watchdog unit 40 may send a command to IMD 12 to cause IMD 12 to stop delivering therapy and/or perform a power-on reset (POR). In some embodiments, watchdog unit 40 or IMD 12 stores a known, safe neurostimulation therapy program. In such embodiments, watchdog unit 40 may provide the program to IMD 12, or send a command to IMD 12 to cause IMD 12 to recall the program for delivery of neurostimulation therapy according to the program.

Programming device 20 sends a stay-alive signal to watchdog unit 40 periodically such that watchdog unit 40 receives a stay-alive signal before the watchdog timer expires. In exemplary embodiments, the stay-alive signals comprise transitions on one or more data lines of cable 28 that couple programming device 20 to watchdog unit 40. By requiring stay-alive signals to be active transitions on one or more data lines rather than passive hardware handshaking lines, watchdog unit 40 may avoid erroneously resetting the watchdog timer in situations where programming device 20 has failed but continues to generate the passive signal, e.g. the signal is "locked in" by failure of programming device 20. Programming device 20 may provide stay-alive signals upon execution of instructions of control software of programming device 20 that is used for transmission of programming commands to IMD 12, rather than as part of an independent thread or process, so that programming device 20 does not continue to signal that it is operating properly despite the fact that the control software has failed.

Watchdog unit 40 receives signals, e.g., programming commands, from programming device 20 via cable 28 during a programming operation, e.g., a reprogramming of IMD 12 with a new program to test during a programming session, that are provided to telemetry head 26 for transmission to IMD 12. In exemplary embodiments, the signals are transitions on one or more data lines of cable 28 that couple programming device 20 to watchdog unit 40. In some embodiments, watchdog unit 40 resets the watchdog timer upon receipt of both programming signals and stay-alive signals, and programming device 20 provides dedicated stay-alive signals such that watchdog unit 40 receives either a programming signal or stay-alive signal before the watchdog timer expires. Programming device 20 may send programming signals and stay-alive signals on common or separate data lines of cable 28.

As described above, a programming session may include multiple programming operations, e.g., IMD 12 may be reprogrammed a number of times to test a number of programs. Further, the programming session may include a period between programming operations where non-critical communication, or no communication, between programming device 20 and IMD 12 is taking place. In order to avoid delivery of stay-alive signals and maintenance of the watchdog timer during periods between programming operations, e.g., non-critical periods, programming device 20 may only deliver stay-alive signals during programming operations, and may signal the beginnings and ends of programming operations to watchdog unit 40 to cause watchdog unit to maintain the watchdog timer only during the programming operations.

As described above, watchdog unit 40 maintains the watchdog timer to detect hardware or software failures of programming device 20, and place IMD 12 in a safe state in response to such a failure. Further, because the watchdog timer will also expire if cable 28 fails, watchdog unit 40 will detect a failure of cable 28, and place IMD 12 in a safe state in response to such a failure.

Figure 3:
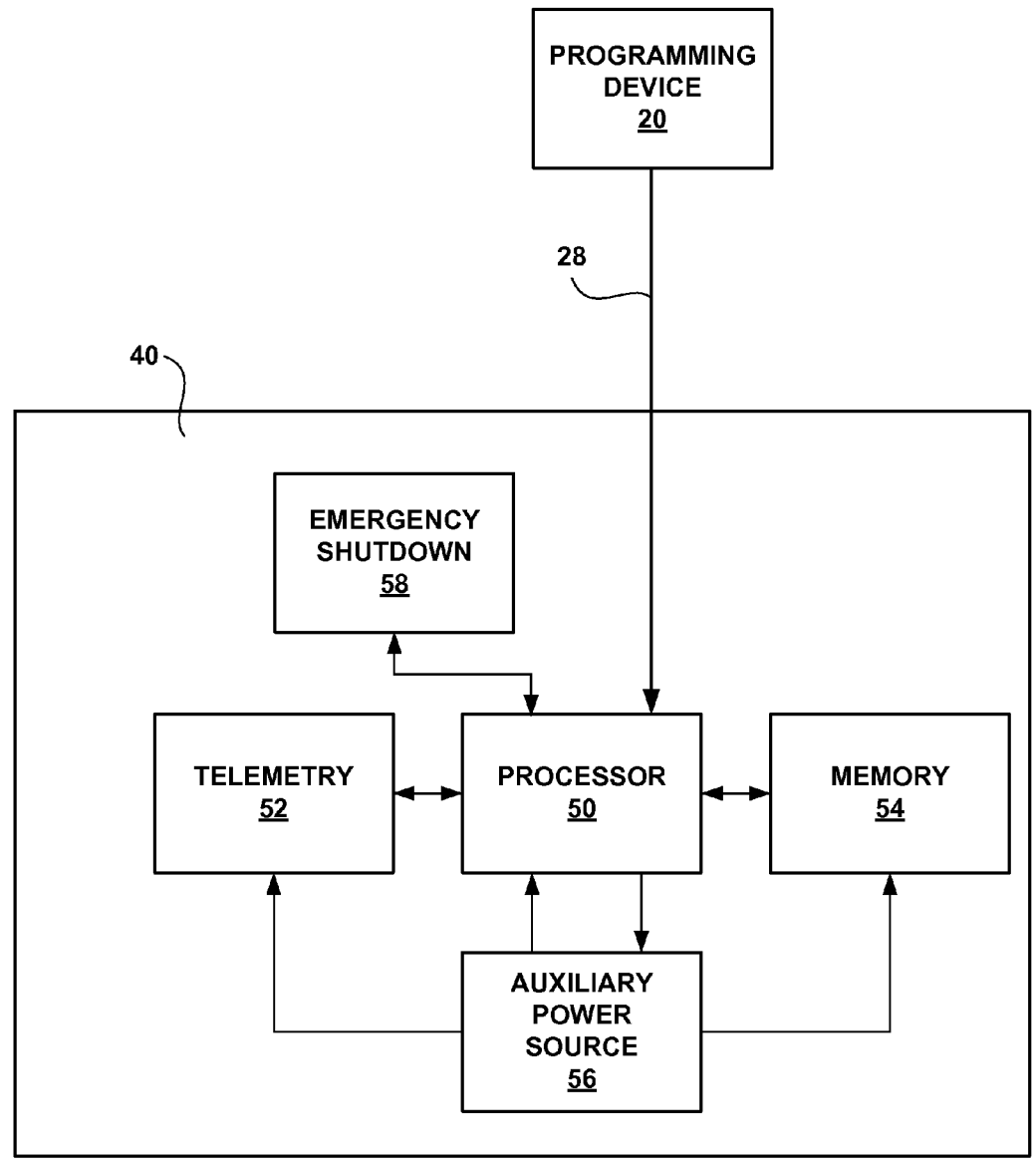
FIG. 3 is a block diagram further illustrating the watchdog unit of FIG. 2 according to an embodiment of the invention.

FIG. 3 is a block diagram further illustrating watchdog unit 40 according to an embodiment of the invention. As illustrated in FIG. 3, watchdog unit 40 includes a processor 50 that controls watchdog unit 40 to provide the functionality attributed to watchdog unit 40 herein. Processor 50 maintains the watchdog timer as described above, and receives programming signals and stay-alive signals from programming device 20 via one or more data lines of cable 28.

Watchdog unit 40 may include a telemetry circuit 52 that enables communication between watchdog unit 40 and IMD 12 (FIG. 1). Upon expiration of the watchdog timer, processor 50 sends a command to IMD 12 via telemetry circuit 52 and telemetry head 26 (FIG. 1) to change a mode of operation of IMD 12, e.g., to place IMD 12 in a known, safe state. As described above, the command may cause IMD 12 to suspend delivery of therapy, perform a POR, and/or recall a stored program. In some embodiments, upon expiration of the watchdog timer, processor 50 sends a program stored in a memory 54 to IMD 12 via telemetry circuit 52 and head 26 to cause IMD 12 to deliver therapy according to the program. During "normal" operation, e.g., when the watchdog timer has not expired, processor 50 sends programming signals received from programming device 20 to IMD 12 via telemetry head 26.

In exemplary embodiments, watchdog unit 40 receives power for operation from programming device 20 via cable 28. In such embodiments, watchdog unit 40 may also include an auxiliary power source 56. In the event that processor 50 detects a failure in the delivery of power from programming device 20, which may be caused by a hardware failure of device 20 or a failure of cable 28, processor 50 may activate auxiliary power source 56 and send a command to IMD 12 via telemetry circuit 52 to change a mode of operation of IMD 12.

Auxiliary power source 56 may be, for example, a rechargeable battery or capacitive element. In some embodiments, auxiliary power source 56 need only store enough power to allow processor 50 to send a command to IMD 12 to place IMD 12 in a known, safe state. Further, the invention is not limited to embodiments where watchdog unit 40 receives primary power from programming device 20, but instead includes embodiments where watchdog unit 40 houses a primary power source, such as a rechargeable or non-rechargeable battery.

In some embodiments, watchdog unit 40 provides an emergency shutdown circuit 58, which may be activated by a user, such as the clinician or patient 14 (FIG. 1). Upon activation of emergency shutdown circuit 58, processor 50 sends a command to IMD 12 via telemetry circuit 52 to cause IMD 12 to, for example, suspend delivery of therapy. Emergency shutdown circuit 58 may include, for example, a switch that is activated by the user pressing a button located on a housing of watchdog unit 40.

Processor 50 may include one or more of a microprocessor, a controller, a digital signal processor (DSP), an application specific integrated circuit (ASIC), a field-programmable gate array (FPGA), discrete logic circuitry, or the like. Memory 54 may store program instructions that cause processor 50 to provide the functionality ascribed to it herein. Memory 54 may include one or more volatile, non-volatile, magnetic, optical, or electrical media, such as read-only memory (ROM), random access memory (RAM), electrically-erasable programmable ROM (EEPROM), non-volatile RAM (NVRAM), flash memory, or the like. Memory 54 may include both on-board and off-board components.

Figure 4:
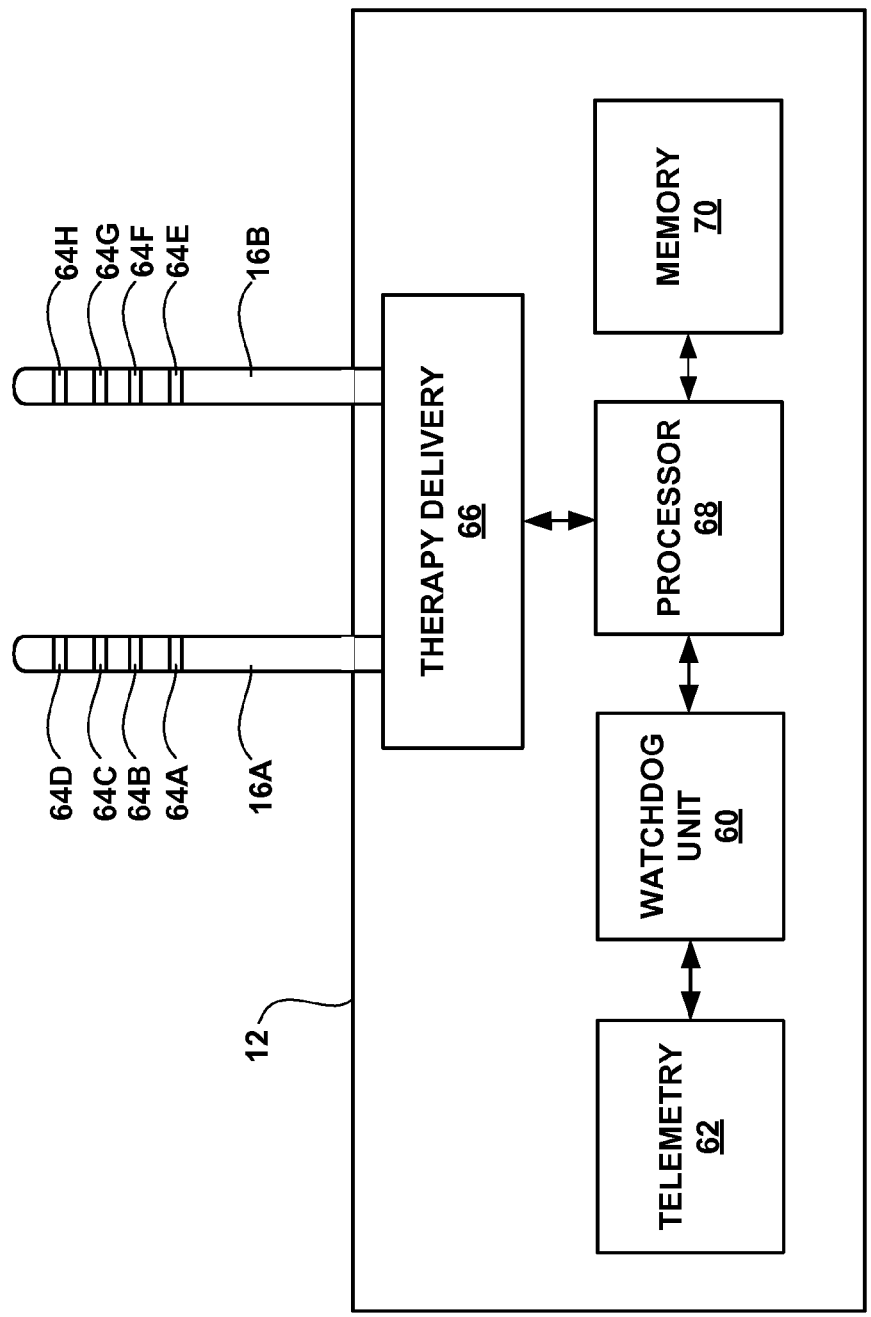
FIG. 4 is a block diagram illustrating the implantable medical device of FIG. 1 according to an embodiment of the invention in which the implantable medical device includes a watchdog unit.

FIG. 4 is a block diagram illustrating IMD 12 according to an embodiment of the invention in which IMD 12 includes a watchdog unit 60. Like watchdog unit 40, watchdog unit 60 receives stay-alive signals from programming device 20, resets a watchdog timer in response to receipt of stay-alive signals, and changes a mode of operation of IMD 12 in response to expiration of the watchdog timer. Watchdog unit 60 located within IMD 12 may detect failure of telemetry head 26 (FIG. 1), loss of the RF telemetry link between programming device 20 and IMD 12, and failure of a telemetry circuit 62 of IMD 12 in addition to hardware or software failures of programming device 20 and failure of cable 28 (FIG. 1).

IMD 12 delivers neurostimulation therapy via electrodes 64A-D of lead 16A and electrodes 64E-H of lead 16B (collectively "electrodes 64"). Electrodes 64 may be ring electrodes. The configuration, type and number of electrodes 64 illustrated in FIG. 2 are merely exemplary.

Electrodes 64 are electrically coupled to a therapy delivery circuit 66 via leads 16. Therapy delivery circuit 66 may, for example, include one or more output pulse generators, e.g., capacitive elements and switches, coupled to a power source such as a battery. Therapy delivery circuit 66 delivers electrical pulses to patient 14 via two or more of electrodes 64 under the control of a processor 68.

As described above, processor 68 controls therapy delivery circuit 66 to deliver neurostimulation therapy according to a program. Specifically, processor 68 may control circuit 66 to deliver electrical pulses with the amplitudes and widths, and at the rates specified by the program. Processor 68 may also control circuit 66 to deliver the pulses via a selected combination of electrodes 64, as specified by the program.

As described above, IMD 12 may be reprogrammed a number of times during a programming session to test a number of programs. For each program tested, IMD 12 receives a number of commands, including the program parameters, from programming device 20 via telemetry circuit 62 and watchdog unit 60. The program parameters are stored within a memory 70 as the program used by processor 68 to control delivery of neurostimulation.

Programming device 20 also sends stay-alive signals via RF device telemetry, which are received by watchdog unit 60 via telemetry circuit 62. Watchdog unit 60 may reset the watchdog timer upon receipt of each stay-alive signal, and may also reset the watchdog timer upon receipt of programming commands from programming device 20. In some embodiments, watchdog unit 60 also receives signals indicating the beginning and ending of a programming operation from programming device 20, and maintains the watchdog timer only during the indicated programming operations.

Watchdog unit 60 changes a mode of operation of IMD 12, e.g., places IMD 12 into a known safe state, upon expiration of the watchdog timer. Watchdog unit 60 may, for example, cause IMD 12 to suspend delivery of therapy, perform a POR, and/or activate a known, safe program stored in memory 70. The functionality attributed to watchdog unit 60 herein may be provided by processor 68, or by a separate processor. Where watchdog unit 60 is embodied within a separate processor, watchdog unit 60 may signal expiration of the watchdog timer to processor 68 to cause processor 68 to change a mode of operation of IMD 12 in any of the above-identified ways.

Processor 68 and watchdog unit 60 may include one or more of a microprocessor, a controller, a DSP, an ASIC, an FPGA, discrete logic circuitry, or the like. Memory 70 may include program instructions that, when executed by processor 68 and watchdog unit 60, cause processor 68 and watchdog unit 60 to perform the functions ascribed to processor 68 and watchdog unit 60 herein. Memory 70 may include one or more volatile, non-volatile, magnetic, optical, or electrical media, such as RAM, ROM, NVRAM, EEPROM, flash memory, and the like. Memory 70 may include on-board and/or off-board components.

Figure 5:
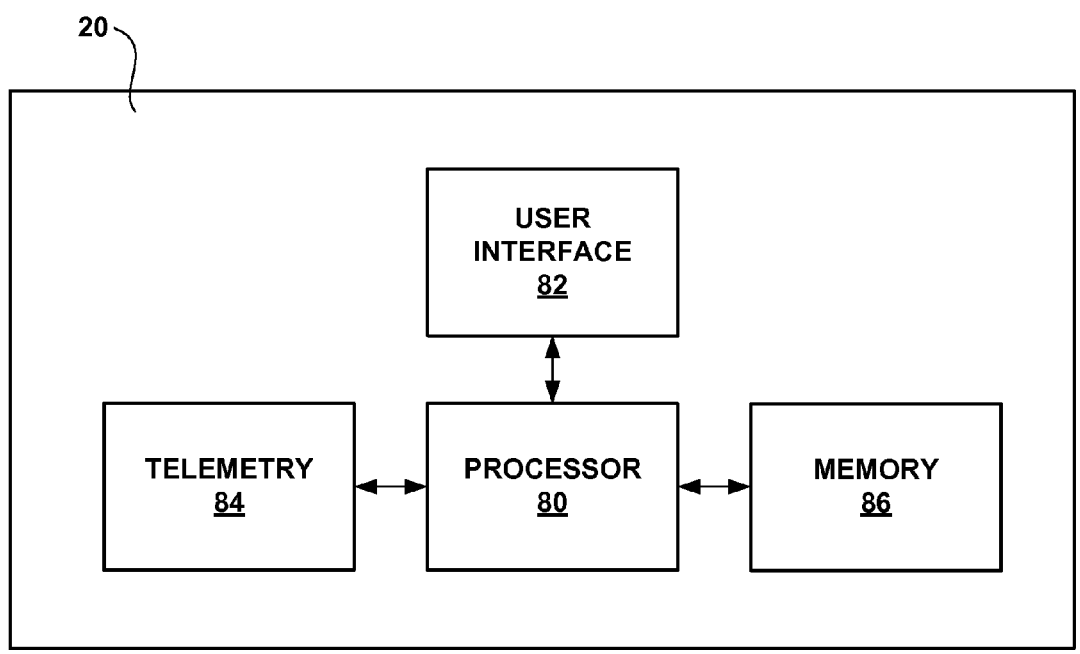
FIG. 5 is a block diagram illustrating an exemplary programming device that facilitates failsafe programming of the implantable medical device of FIG. 1.

FIG. 5 is a block diagram illustrating programming device 20 in greater detail. Programming device 20 includes a processor 80 and a user interface 82 that allows a user, such as the clinician or patient 14, to interact with processor 80. User interface 82 may include display 22 and keypad 24 (FIG. 1), and allow the user to, for example, select programs to test during a programming session.

Processor 80 may transmit programming signals, e.g., commands, to IMD 12 via a telemetry circuit 84 and telemetry head 26 (FIG. 1). Processor 80 also provides stay-alive signals to a watchdog unit 40 via a data line of cable 28 (FIG. 1), or to a watchdog unit 60 via telemetry circuit 84 and telemetry head 26, as described above. Processor 80 sends the stay-alive signals periodically, such that the watchdog unit 40, 60 receives a stay-alive signal before the watchdog timer expires.

In some embodiments, as described above, the watchdog unit 40, 60 resets the watchdog timer upon receipt of both programming signals and stay-alive signals, and processor 80 provides dedicated stay-alive signals such that the watchdog unit 40, 60 receives with a programming signal or stay-alive signal before the watchdog timer expires. In exemplary embodiments, processor 80 provides stay-alive signals upon execution of instructions of control software of programming device 20. Further, in order to avoid delivery of stay-alive signals during period where there is no communication or non-critical communication with IMD 12, processor 80 may send signals to the watchdog unit 40, 60 indicating the beginning and end of programming operations within a programming session, and may send stay-alive signals only during the programming operations.

Processor 80 may include a microprocessor, a controller, a DSP, an ASIC, an FPGA, discrete logic circuitry, or the like. A memory 86 may include program instructions that, when executed by processor 80, cause programming device 20 to perform the functions ascribed to programming device 20 herein. Memory 86 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 6:
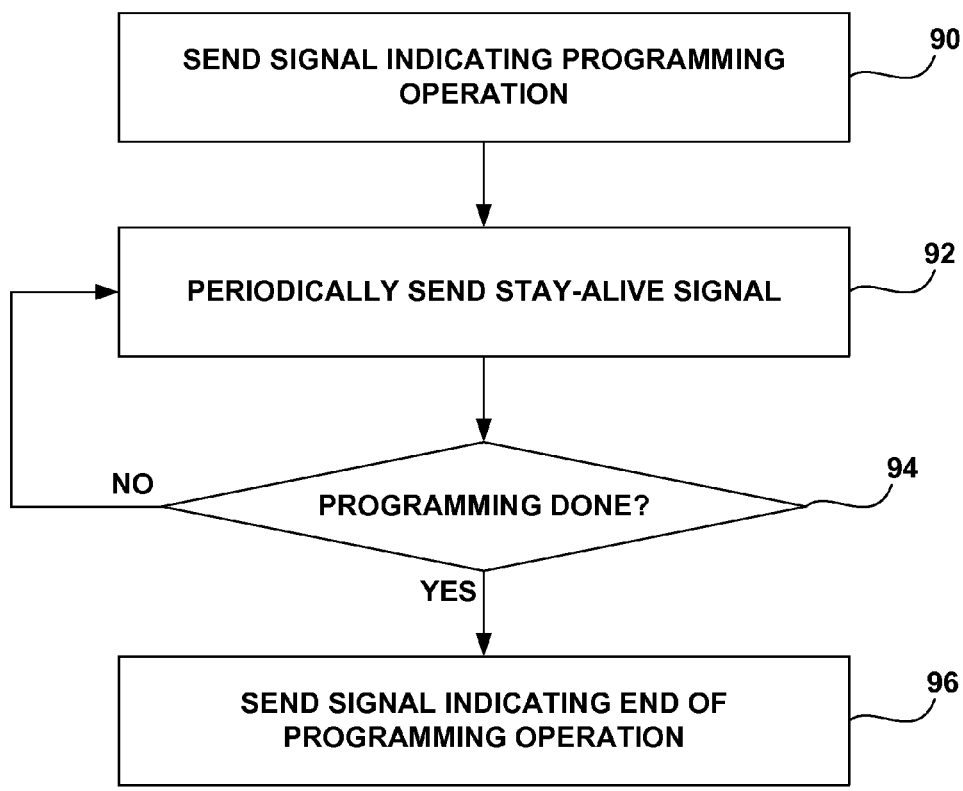
FIG. 6 is a flow diagram illustrating exemplary operation of the programming device of FIG. 5 to facilitate failsafe programming of the implantable medical of FIG. 1.

FIG. 6 is a flow diagram illustrating exemplary operation of programming device 20 to facilitate failsafe programming of IMD 12. Programming device 20 sends a signal indicating the beginning of a programming operation to a watchdog unit 40, 60 (90). During the programming operation, programming device 20 periodically sends stay-alive signals to the watchdog unit 40, 60 to cause the watchdog unit to reset a watchdog timer (92). In some embodiments, programming device 20 may only send dedicated stay-alive signals when no programming signal has been sent in time to cause the watchdog unit 40, 60 to reset the watchdog timer. When programming device 20 determines that the programming operation is done (94), programming device 20 sends a signal to the watchdog unit 40, 60 indicating the end of the programming operation (96).

Figure 7:
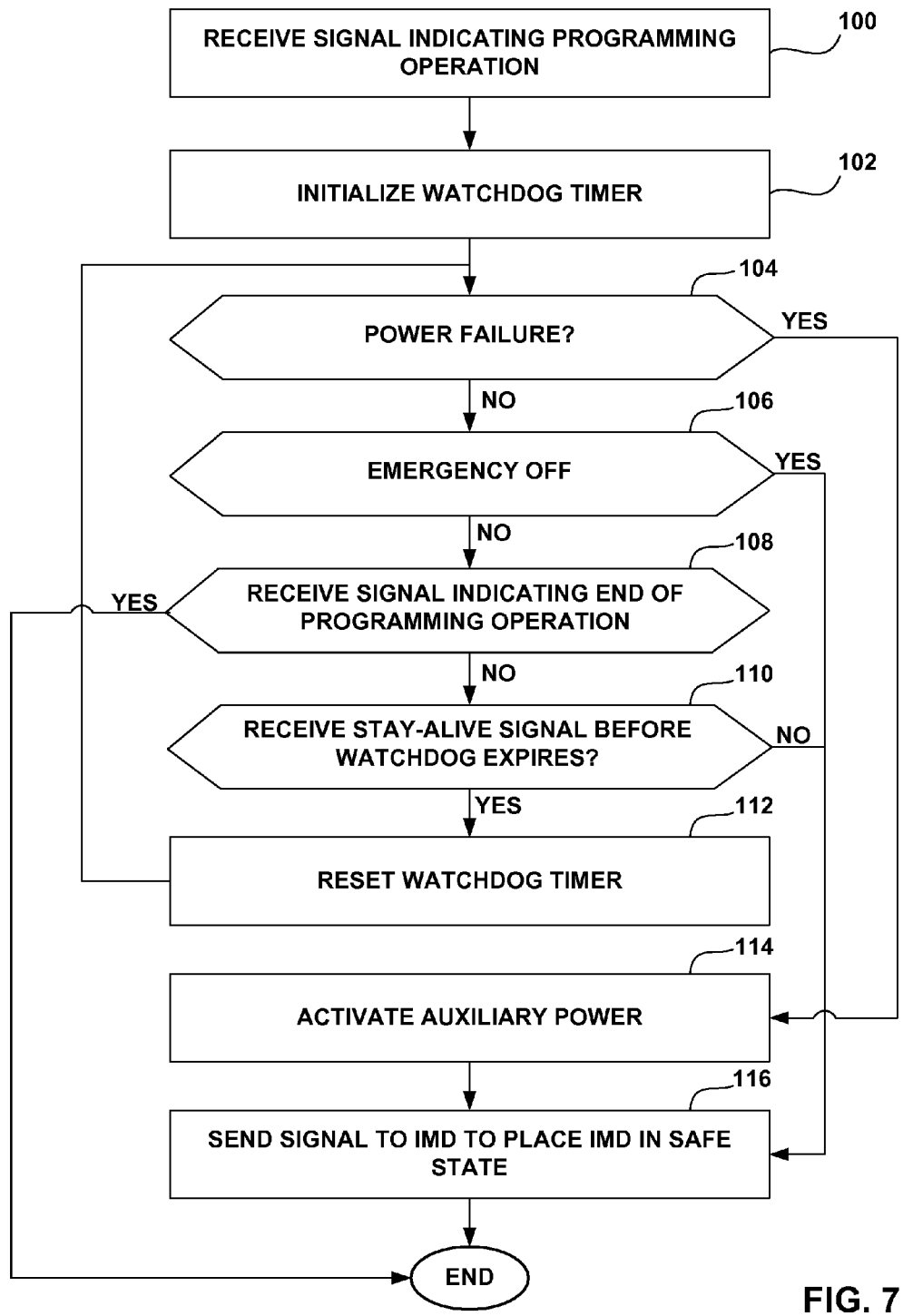
FIG. 7 is a flow diagram illustrating exemplary operation of the watchdog unit of FIG. 3 to facilitate failsafe programming of the implantable medical device of FIG. 1.

FIG. 7 is a flow diagram illustrating exemplary operation of watchdog unit 40 to facilitate failsafe programming of IMD 12. Although FIG. 7 illustrates operation of watchdog unit 40, it is understood that watchdog unit 60, as described above, may perform many of the functions of watchdog unit 40.

Watchdog unit 40 receives a signal indicating the start of a programming operation from programming device 20 via one or more data lines of cable 28 (100), and initializes a watchdog timer in response to the signal (102). Watchdog unit 40 monitors for failure of power delivery from programming device 20 (104), activation of an emergency shutdown circuit 58 by a user (106), a signal indicating the end of the programming operation from programming device 20 (108), and stay-alive signals from programming device 20 (110) during the programming operation. Each time watchdog unit 40 receives a stay-alive signal, and in some embodiments a programming signal, from programming device 20 before the watchdog timer expires, watchdog unit 40 resets the watchdog timer (112).

If watchdog unit 40 does not receive a stay-alive signal or programming signal from programming device 20 before the watchdog timer expires (110), watchdog unit sends a signal to IMD 12 via telemetry head 26 to place IMD 12 in a known, safe state (116). The signal may cause IMD 12 to, for example, suspend delivery of therapy, perform a POR, and/or recall a known, safe therapy program. Watchdog unit 40 also sends such a signal to IMD 12 (116) if a user activates the emergency shutdown circuit 58 (106). In embodiments wherein watchdog unit 40 receives primary power from programming device 20, watchdog unit 40 activates an auxiliary power source 56 (114) and sends the signal to IMD 12 (116) upon detection of a failure of power delivery by programming device 20 (104). When watchdog unit 40 receives a signal from programming device 20 indicating the end of the programming operation (108), watchdog unit 40 may stop maintaining the watchdog timer.

Various embodiments of the invention have been described. However, one skilled in the art will recognize the various modifications may be made to the described embodiments without departing from the scope of the invention. For example, the invention is not limited to programming of spinal cord stimulation (SCS) therapy, or even to programming of neurostimulation therapy. The failsafe programming techniques described herein may be applied to the programming of any implantable medical device, such as pacemakers and implantable pumps. Moreover, the invention is not limited to failsafe programming of implantable medical devices that deliver therapy, but may include failsafe programming of implantable medical devices used to monitor patients, such as implantable hemodynamic monitors or loop recorders.

Further, although a programming device has been described herein primarily as a clinician programmer used to program therapy during a programming session, the invention is not so limited. A programming device that facilitates failsafe programming of an implantable medical device may a patient programmer used to control delivery of therapy by an implanted medical device in an ambulatory setting. For example, a patient programmer may be used to adjust program parameter for delivery of neurostimulation by an implantable medical device. These and other embodiments are within the scope of the following claims.

The invention claimed is:

1. A method comprising:
    receiving stay-alive signals from a programming device at a watchdog unit coupled to the programming device during a programming session between the programming device and an implantable medical device;
    resetting a watchdog timer maintained by the watchdog unit in response to receipt of each of the stay-alive signals; and
    sending a signal from the watchdog unit to the implantable medical device via wireless telemetry to cause the implantable medical device to revert to a program previously stored within a memory of the implantable medical device in response to expiration of the watchdog timer.

2. The method of claim 1, wherein receiving stay-alive signals comprises detecting transitions on a data line that couples the watchdog unit to the programming device.

3. The method of claim 1, wherein receiving stay-alive signals comprises receiving stay-alive signals via wireless telemetry.

4. The method of claim 1, wherein receiving stay-alive signals comprises receiving programming signals and stay-alive signals, and resetting a watchdog timer comprises resetting the watchdog timer in response to each of the programming signals and stay-alive signals.

5. The method of claim 1, further comprising:
receiving a signal at the watchdog unit, from the programming device, that indicates initiation of a programming operation; and
initializing the watchdog timer in response to the signal.

6. The method of claim 1, further comprising:
receiving, at the watchdog unit, power from the programming device;
detecting, at the watchdog unit, a failure of power delivery by the programming device;
activating an auxiliary power source of the watchdog unit in response to the detection; and
changing the mode of operation of the implantable medical device using the watchdog unit in response to the detection.

7. A system comprising:
an implantable medical device; and
a watchdog unit to receive stay-alive signals during a programming session with the implantable medical device, reset a watchdog timer maintained by the watchdog unit in response to receipt of each of the stay-alive signals, and send a signal to the implantable medical device via wireless telemetry to cause the implantable medical device to revert to a program previously stored within a memory of the implantable medical device in response to expiration of the watchdog timer.

8. The system of claim 7, further comprising a programming device and a cable, wherein the watchdog unit is coupled to the programming device via a data line of the cable, and receives stay-alive signals from the programming device by detecting transitions on the data line.

9. The system of claim 7, further comprising a programming device, wherein the watchdog unit receives a signal from the programming device that indicates initiation of a programming operation, and initializes the watchdog timer in response to the signal.

10. The system of claim 7, further comprising a programming device, wherein the watchdog unit receives power from the programming device, the watchdog unit further comprising an auxiliary power source, and
wherein the watchdog unit detects a failure of power delivery by the programming device, activates the auxiliary power source in response to the detection, and sends a signal to the implantable medical device via wireless telemetry to cause the implantable medical device to revert to the program previously stored within the memory of the implantable medical device in response to the detection.

11. The system of claim 7, wherein the watchdog unit further comprises a user interface, receives an emergency-off signal in response to interaction of a user with the user interface, and sends a signal to the implantable medical device via wireless telemetry to cause the implantable medical device to revert to the program previously stored within the memory of the implantable medical device in response to receipt of the signal.

12. The system of claim 7, wherein the implantable medical device comprises an implantable neurostimulator.

\* \* \* \* \*